(12) United States Patent
Wilkinson

(10) Patent No.: US 6,571,735 B1
(45) Date of Patent: Jun. 3, 2003

(54) NON-METALLIC BIOREACTOR AND USES

(76) Inventor: Loy Wilkinson, 250 Northrup St., Bridgewater, CT (US) 06752

( * ) Notice: Subject to any disclaimer, the term of this patent is extended or adjusted under 35 U.S.C. 154(b) by 0 days.

(21) Appl. No.: 09/684,916

(22) Filed: Oct. 10, 2000

(51) Int. Cl.$^7$ .................................................. A01K 29/00
(52) U.S. Cl. ........................................................ 119/215
(58) Field of Search ........................... 435/292.1, 296.1, 435/297.2, 304.1; 119/215, 224, 226, 245

(56) References Cited

U.S. PATENT DOCUMENTS

| | | | |
|---|---|---|---|
| 301,285 A | 7/1884 | Schmitz | |
| 3,661,262 A | 5/1972 | Sanders | 210/169 |
| 3,763,824 A | 10/1973 | Schoon | 119/4 |
| 3,870,020 A | 3/1975 | Hunt | 119/4 |
| 3,958,364 A | 5/1976 | Schneck et al. | 47/1.4 |
| 3,969,844 A | 7/1976 | Fogel et al. | 47/58 |
| 4,005,546 A | 2/1977 | Oswald | 47/1.4 |
| 4,043,903 A | 8/1977 | Dor | 210/22 |
| 4,065,875 A | 1/1978 | Srna | 47/1.4 |
| 4,080,930 A | 3/1978 | Pruder et al. | 119/4 |
| 4,137,868 A | 2/1979 | Pryor | 119/2 |
| 4,235,934 A | 11/1980 | Egli et al. | 426/43 |
| 4,236,349 A | 12/1980 | Ramus | 47/1.4 |
| 4,253,271 A | 3/1981 | Raymond | 47/1.4 |
| 4,267,038 A | 5/1981 | Thompson | 210/602 |
| 4,276,384 A | 6/1981 | Mueller | 435/311 |
| 4,320,594 A | 3/1982 | Raymond | 47/1.4 |
| 4,324,067 A | 4/1982 | Kessler | 47/1.4 |
| 4,324,068 A | 4/1982 | Anthony | 47/1.4 |
| 4,354,936 A | 10/1982 | Ishida et al. | 210/602 |
| 4,431,738 A | 2/1984 | Maeda et al. | 435/240 |
| 4,442,211 A | 4/1984 | Greenbaum | 435/168 |
| 4,468,460 A | 8/1984 | Kumamoto | 435/240 |
| 4,533,548 A | 8/1985 | Umezawa et al. | 514/54 |
| 4,699,086 A | 10/1987 | Mori | 119/3 |
| 4,699,087 A | 10/1987 | Mori | 119/3 |
| 4,798,168 A | 1/1989 | Vadseth et al. | 119/3 |
| 4,874,695 A | 10/1989 | Pincus | 435/19 |
| 4,994,280 A | 2/1991 | Kochinsky | 424/672 |
| 5,071,760 A | 12/1991 | Watanabe et al. | 435/240.25 |
| 5,081,036 A * | 1/1992 | Familletti | 435/286.7 |
| 5,176,100 A | 1/1993 | Fujino | 119/3 |
| 5,225,346 A | 7/1993 | Matsumiya et al. | 435/284 |
| 5,350,080 A | 9/1994 | Brown et al. | 220/465 |
| 5,362,642 A | 11/1994 | Kern | 435/240.1 |
| 5,441,877 A | 8/1995 | Chiaffredo et al. | 435/176 |
| 5,447,629 A * | 9/1995 | Chaumont et al. | 210/150 |
| 5,449,617 A | 9/1995 | Falkenberg et al. | 435/240.25 |
| 5,492,938 A | 2/1996 | Kyle et al. | 514/786 |
| 5,518,990 A | 5/1996 | Ushio et al. | 504/121 |
| 5,686,304 A | 11/1997 | Codner | 435/325 |
| 5,692,455 A | 12/1997 | Wang | 119/242 |
| 5,711,983 A | 1/1998 | Kyle et al. | 426/635 |
| 5,766,875 A | 6/1998 | Hafeman et al. | 435/29 |
| 5,837,638 A | 11/1998 | V-Derstok et al. | 502/62 |
| 5,866,150 A | 2/1999 | Wang | 424/405 |
| 5,897,997 A * | 4/1999 | Louvel | 435/294.1 |
| 5,939,313 A * | 8/1999 | Cheng | 261/121.1 |
| 5,961,831 A | 10/1999 | Lee et al. | 210/614 |
| 5,985,649 A * | 11/1999 | Stensel et al. | 435/266 |
| 6,087,158 A * | 7/2000 | Worden et al. | 422/140 |
| 6,245,555 B1 * | 6/2001 | Curtis | 220/495.05 |
| 6,326,191 B2 * | 12/2001 | VanToever | 210/167 |
| 6,348,347 B1 * | 2/2002 | Hirabayashi et al. | 239/229 |

* cited by examiner

*Primary Examiner*—Thomas Price
(74) *Attorney, Agent, or Firm*—Fitzpatrick, Cella, Harper & Scinto

(57) ABSTRACT

An autoclavable unicellular culture system comprising flexible, light transmitting walls, an internal oxygen diffuser and a head plate which has a plurality of apertures. The present invention also comprises a fish or shellfish rearing system incorporating the culture system.

15 Claims, 4 Drawing Sheets

NON-METALLIC BIOREACTOR AND USES

FIELD OF THE INVENTION

Figure 1:
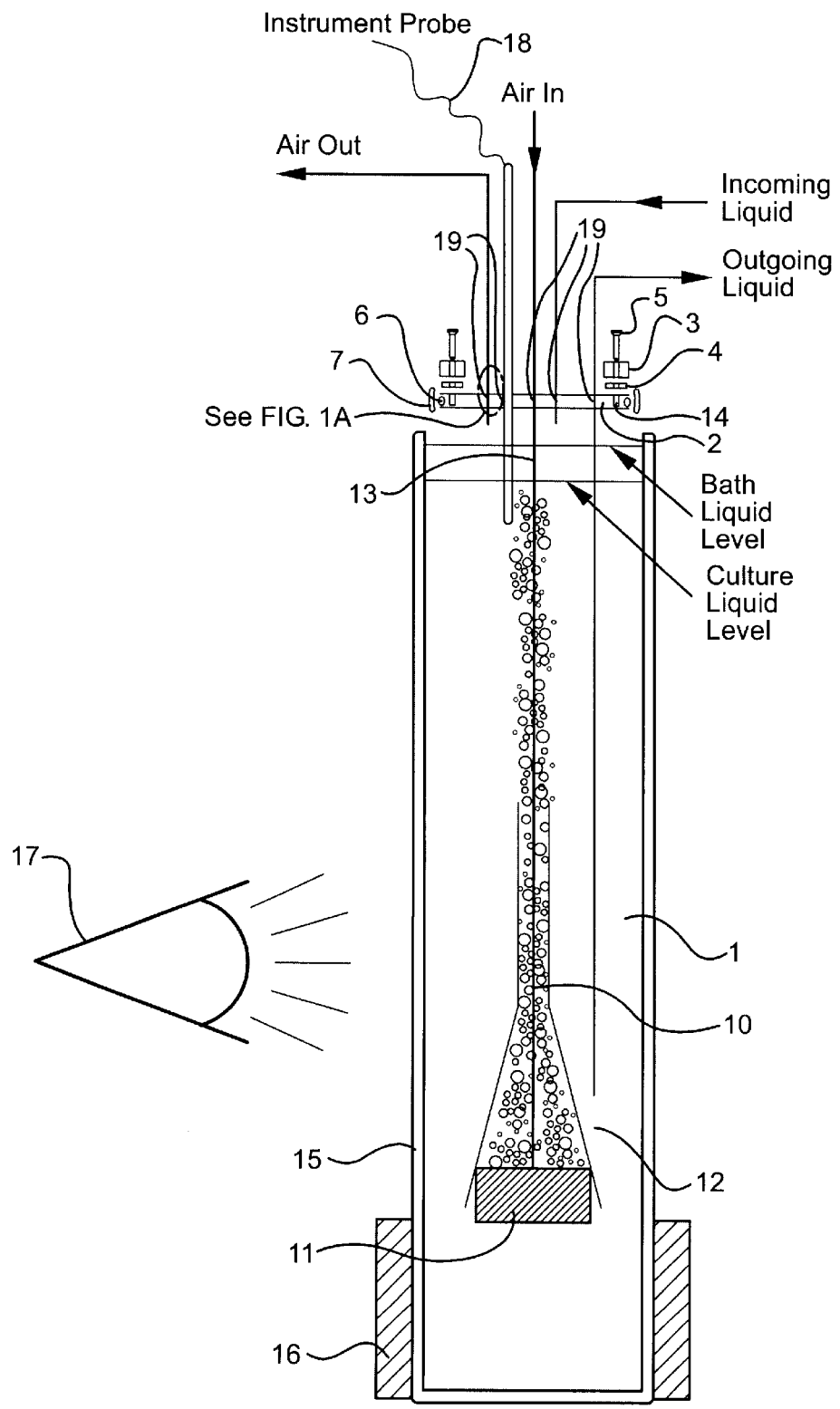

This invention relates to flexible, autoclavable bioreactors and aquaculture systems incorporating said bioreactors.

BACKGROUND OF THE INVENTION

A sterilizable, non-metallic bioreactor which is low cost, has utility in the production of autotrophic, mixotrophic and heterotrophic cell cultures and which can be incorporated into a wide range of bioprocessing systems. The bioreactor can be used, for example, for cell growth with subsequent extraction of cell components and also for applications that utilize the whole cell such as for the production of protein or for the production of algae for aquaculture.

In the pharmaceutical and food processing industries unicellular organisms are generally produced in commercial quantities using metallic bioreactors or using non-metallic systems that employ sterile plastic bags. Sterile plastic bag bioreactors may optionally be supported by an apparatus designed to rock the bag and mix its contents. In certain circumstances it is also possible to produce unicellular organisms in non-sterile bags.

Metallic systems are too expensive to be a viable method for commercial applications in agriculture and aquaculture. Rocking bag systems are also too costly for agriculture and aquaculture, and are limited in the extent to which they can be scaled up. Non-sterile bag systems cannot be used for mixotrophic (a heterotrophic reaction that is subject to photonic radiation) or heterotrophic cell culture because of the presence of bacteria that compete for the preferred food, soluble organic chemicals. Therefore, cell production utilizing non-sterile bags is restricted to autotrophic and photo autotrophic systems where significant quantities of soluble organic chemicals are not used as a source of nutrients. Photo autotrophic systems that employ artificial light as the energy source are inefficient and not cost effective and are therefore limited to commercial applications where the cost of cell production is not an important factor.

A practical, efficient bioreactor will find many applications in commercial microbiology and in new applications in agriculture and aquaculture. On-site production of unicellular food for animals is currently impractical because the commercial systems now in use for cell growth are too expensive for agriculture or aquaculture applications. The systems now in use are either glass-lined or stainless steel systems.

Rearing systems for zooplankton, shellfish and fish are well known and numerous versions of such systems are described in the literature. See, for example, U.S. Pat. No. 5,176,100. Rearing systems all have the same general requirements. One requirement is to reduce the concentrations of toxic metabolites in the water, for example ammonia. This requirement is generally met utilizing a biofilter through which the contaminated water is circulated and where the water is contacted with a stream of air. Nitrifying and other bacteria reside in the biofilter and serve to convert ammonia to less toxic nitrate and reduce the concentration of dissolved organic compounds. Alternatively, inorganic materials may be absorbed by zeolite or activated carbon, followed by contact with air or oxygen. Problems with the methods that employ absorption techniques include clogging of the filters and an insufficient contact of the unwanted materials with the oxygen.

A second requirement of a rearing system is the need for a high level of dissolved oxygen. This is commonly achieved by bubbling air or oxygen into the rearing tank water or through the use of an oxygen permeable bag systems as disclosed in U.S. Pat. No. 5,225,346.

A third requirement is the need to expeditiously remove solid waste materials because accumulations of solid waste can harbor colonies of toxic anaerobic bacteria. In existing systems solid wastes are generally removed through a connection in the bottom of the tank. The current systems often use grain-based nutrients. The problem with use of such systems is that grain-based foods result in solid wastes that contain lignin and highly oriented cellulose which are difficult to convert to algae nutrient or to any other practical use. Algae are the natural food for shellfish and zooplankton and, further, zooplankton is a natural food for fish and crustaceans. These natural foods create waste that may be catabolized by various enzymes that are common in nature, especially at the bottom of marine environments.

A fourth requirement of an efficient rearing system is the need to counter the build-up of nitrate in the rearing tank. In the past, this has usually been accomplished by purging the tank and thereafter discharging the purge into a waterway causing pollution.

One of the technological obstacles to the production of single-cell algae as a nutrient source is the need to separate the algae harvest from the culture. This obstacle is often overcome with techniques such as centrifugation, flocculation, reverse osmosis, etc. A continuous culture system integrated with rearing systems would provide significant efficiency benefits by eliminating the need to separate the cells from the media.

A variety of animal cell types can also be grown in culture, including connective tissue cells, skeletal, cardiac, and epithelial cells, neural cells, endocrine cells, melanocytes, and many types of tumor cells. Similarly a variety of growth media can be used, depending on the particular growth requirements of the cells and the growth conditions.

Animal cell culture systems can have a variety of configurations. Depending on the type of cells, their intended use, and the conditions of growth. Most cultures are propagated in the form of a monolayer, with the cells anchored to a glass or plastic substrate. Some, however, are preferably grown in suspension, which has the advantage of simpler propagation. Using a suspension system, subcultures can be made by simple dilution rather than by detaching (e.g., by trypsinization) the cells from anchored growth. Growth in suspension also provides increased surface area with increased bulk, as well as improved ease of harvesting, and the possibility of achieving a "steady state" culture.

Cell growth kinetics in suspension cultures can be affected by a number of considerations. Varying growth conditions such as the growth temperature, initial growth phase of cells, inoculation density, mixing rate, and medium surface area can have important effects. The selection of medium, nutrients, and pH all affect growth in a generally predictable, controllable manner. The ability to supply sufficient oxygen is particularly important and difficult in animal cell culture systems.

SUMMARY OF THE INVENTION

The present invention relates to an autoclavable, unicellular culture system comprising flexible, light transmitting walls, an internal oxygen diffuser, and a head plate which has a plurality of apertures.

The present invention further relates to a fish or shellfish rearing system incorporating the culture system.

A BRIEF DESCRIPTION OF THE DRAWINGS

FIG. 1 is a cross-sectional view of the bioreactor, its inlet and outlet connections, its head plate assembly, its air diffusion apparatus, its heating or cooling element, its vessel with supporting bath and an external source of artificial light.

Figure 1A:
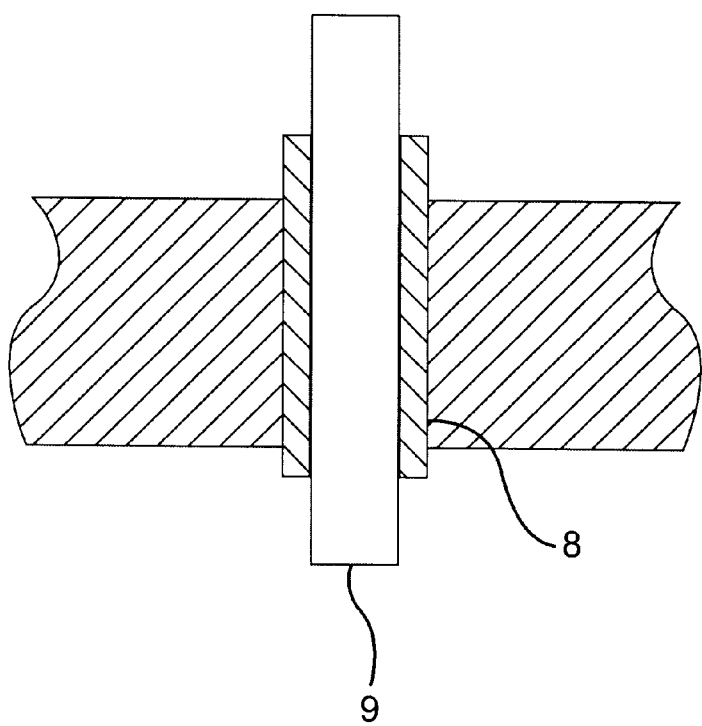

FIG. 1A is an aperture detail of the cross-section of the head plate 2, showing flexible tubing 8 and nipple 9.

Figure 2:
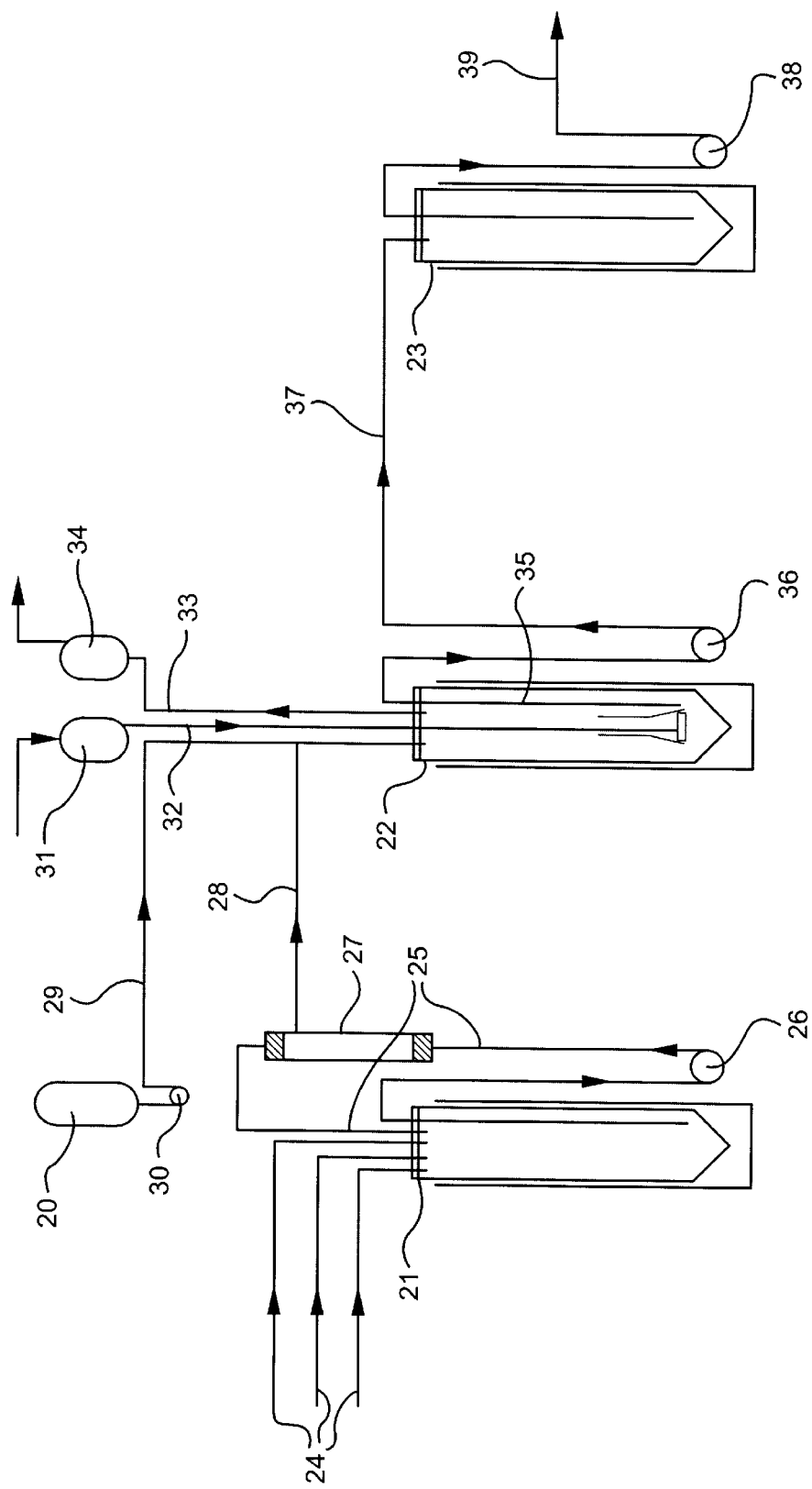

FIG. 2 is a schematic flow diagram of a cell production system that employs the bag design for the bioreactor and ancillary vessels.

Figure 3:
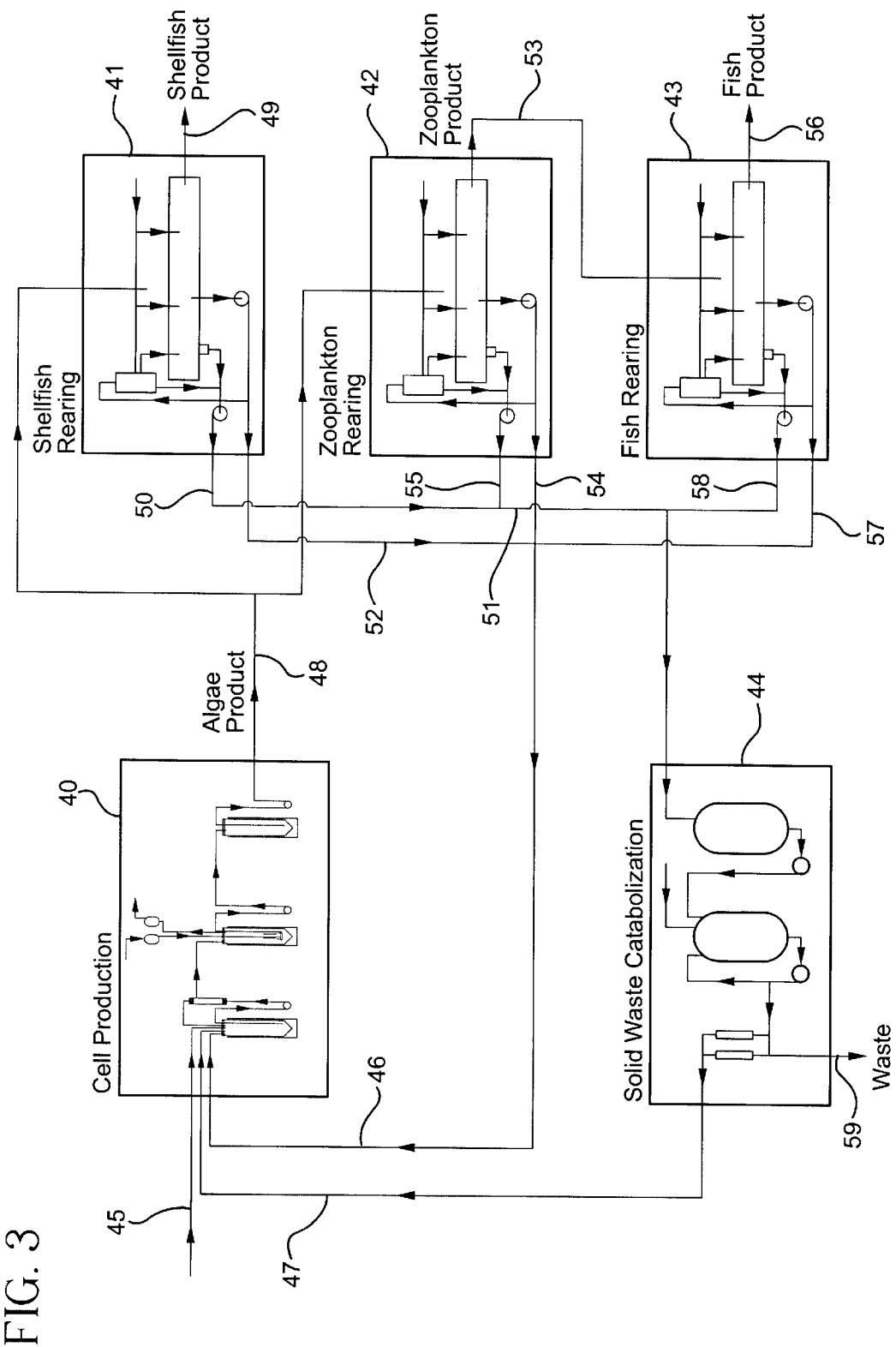

FIG. 3 is a schematic flow diagram of a system that employs the cell production system to produce algae for the production of zooplankton, shellfish and fish in conventional rearing tank systems. The means by which water purges of the rearing tanks and recycled to the algae production system is illustrated. The means by which the production of solid wastes are reduced and converted to nutrient for algae is illustrated.

DETAILED DESCRIPTION OF THE INVENTION

This invention overcomes the limitations of existing culture systems and provides the means to efficiently produce unicellular organisms as a nutrient source for applications in agriculture and aquaculture. The present invention may also find application in the culture of animal cells. The present invention comprises a plastic, sterilizable bioreactor that is easily assembled utilizing readily available materials. Once assembled, the bioreactor may be sterilized by autoclaving and thereafter operated in a sterile condition for 6 months or more under autotrophic, photo autotrophic, mixotrophic or heterotrophic conditions. The bioreactor can be operated in batch, semibatch or continuous modes. A bioreactor operated in batch mode is first charged with media and an inoculum of cells, then air is introduced on a continuous basis as required. Cells multiply and the cell density is increased until a nutrient in the media is depleted. Then the cells are harvested and the process is repeated.

A bioreactor operated in a semibatch mode deviates from the batch mode in that, at the harvest a portion of cells are held in the bioreactor to inoculate the subsequent growth cycle. Commonly, the volume of cells remaining in the bioreactor amount to one-third to two-thirds of the bioreactor volume. A bioreactor operated in continuous mode is harvested continuously at the rate the cells are produced in the bioreactor. The harvest volume is continuously made up with fresh media that is added to the bioreactor. The bioreactor of the present invention can be operated under a range of hydrostatic loads and provides a means of closely controlling the culture temperature. The bioreactor can be incorporated into a processing system working in concert with other equipment commonly used in bioprocessing.

The invention further comprises a bag system bioreactor which can be scaled up from smaller than 1 liter to larger than 1000 liters. A preferred bioreactor according to the current invention, used for algae growth, is approximately 90 liters in volume. Particularly preferred bioreactors according to the invention comprise a tall thin bag system.

One embodiment of the present invention comprises a light transmitting plastic bag preferably sealed on the sides and bottom and open on the top. The top opening is fitted with a head plate which provides multiple apertures for inputting air and media, and for removing air and for harvesting algae culture. Apertures can be provided for insertion of instrument probes.

A further embodiment of the invention comprises a bag system into which gas diffusion system is placed prior to sterilization. During operation of this embodiment of the invention the air diffusion system is situated at the bottom of the bioreactor so that the media is saturated with air. The very fine bubbles produced by the system also prevent the cells from settling and therefore facilitate the harvest of said cells. In a preferred embodiment of the invention the air diffusion system comprises a shroud with a standpipe which directs the flow of bubbles upward, inducing circulation of the liquid which is impelled by the rising bubbles. Spent air containing carbon dioxide breaks from the liquid surface and exits the bioreactor through a connection in the top plate.

In a preferred embodiment of the bioreactor the light transmitting bags are composed of gas-impermeable plastic greater than $2/1000$ of an inch in thickness and preferably at least $4/1000$ of an inch in thickness. In a further preferred embodiment, the open section of the bag is contacted with the head plate. The head plate may be fixed to the bag with a ring and sealed with a gasket. Air may be introduced into the bioreactor through a connection in the head plate. Introduced air travels down through tubing to a diffuser which breaks it into fine bubbles.

In a further embodiment of the invention the bag assembly may be supported by a fluid bath contained in a vessel that is designed to withstand the hydrostatic pressure of the bath. Another aspect of the invention provides temperature control of the bioreactor by controlling the temperature of the external fluid bath. The temperature of the bath may be controlled by an external heater or cooler with circulation of the bath fluid or by heating or cooling elements submerged in the bath or fixed to the outside of the support vessel. For mixotrophic bioreactions, the vessel is constructed of a material permeable to photonic radiation such as a clear reinforced polyester polymer. A system which comprises such a support vessel may be scaled up to 1000 L or more.

A further embodiment of the invention comprises an aquaculture system that simulates the food-fish-waste cycle that is a simplified version of the natural cycle. A key component of the aquaculture system may be a bioreactor which converts the waste of animals grown in the system into nutrients for unicellular organisms which are in turn used as a nutrient source for the animals.

There are three basic steps to the natural food-fish-waste cycle. First, algae grow by photosynthesis utilizing carbon dioxide and nutrients in the water. Second, shellfish grow by consuming the algae and other types of fish grow by consuming algae and zooplankton which also feed on the algae. Both shellfish and fish produce solid and water-soluble wastes. Third, solid wastes are catabolized principally by various benthic enzymatic treatments thereby creating nutrients for algae. The water-soluble wastes created by shellfish and fish also provide nutrients for algae growth.

The steps of the natural cycle may be incorporated into an embodiment of the present invention as a commercial food-fish-waste processing system which produces either shellfish or fish. The system may incorporate a cell production system that comprises a bioreactor which produces unicellular organisms, for example, algae. In a further embodiment of the invention, the components of the food-fish-waste system may be:

1) an algae production system including a bioreactor according to the invention, operating in a mixotrophic mode, vessels to contain bioreactor feeds, vessels to contain the algae product, microporous filters to sterilize the feeds and microporous filters to sterilize the incoming air;

2) a zooplankton, for example Artemia, rearing system including at least one rearing tank, a means to aerate the tank water, a means to circulate the tank water through a biofilter which converts toxic ammonia to less toxic nitrate and filters to remove the solid waste, wherein the algae of the algae production system (step 1) are used as a nutrient source for said zooplankton;

3) a shellfish or fish rearing system including at least one rearing tank to contain the animals, a means to aerate the tank water, a means to circulate the tank water through a biofilter, a biofilter to convert toxic ammonia into less toxic nitrate and filters to remove the solid waste produced by the animals, wherein the shellfish or fish feed on the algae and/or the zooplankton of steps 1 and 2; and 4) a catabolization system that converts the solid waste into water-soluble compounds utilizing enzymatic and acid treatments.

The water-soluble compounds formed by the catabolization system may be used to nourish the algae, thus providing a closed system.

In a preferred embodiment of the invention the algae are suitable for use in a food-fish-waste cycle. Preferred algae include algae that contain a high percentage of polyunsaturated fatty acids. A high percentage of polyunsaturated fatty acid may be achieved by a mixotrophic mode of culture which includes photonic radiation which is known to improve yields of desirable polyunsaturated fatty acids. Examples of preferred algae according to the present invention include Crypthecodiium, Nitzchia, Chlorella and Tetraselmis. In a particularly preferred embodiment the algae is *Tetraselmis chuii*. In a further particularly preferred embodiment the algae is the *Tetraselmis chuii* strain designated P-429 by the National Marine Fisheries Service.

In a preferred embodiment of the invention a single strain of algae is used. In this embodiment, bacteria, fungi and competing algae must be excluded from the system. In another preferred embodiment the water-soluble nutrients produced in the catabolization system are utilized as a nutrient source for the algae. Such an embodiment requires that the recycled materials be blended with fresh nutrients in order to provide a constant media composition. A constant media composition facilitates high algae yields.

While the present invention contemplates growing any fish or shellfish, preferred fish include *Penaeus vannamei* and *Penaeus monodon* and preferred shellfish include *Crossostrae Virginicus, Crossotrae gigas, Pinctada maxima, Pinctada margaritifera, Pinctada fucata,* and *Argopectin irradians*.

A further preferred embodiment of the present invention comprises a three-container, or vessel, production system. In the first container recycled nutrients are mixed with fresh nutrient to formulate the desired eludate composition to add to the culture. The contents of the first container may be mixed by an external circulation pump. A microporous filter, preferably a hollow fiber type filter, may be placed in the circulating loop to provide a microorganism-free feed to a second container, the bioreactor. The bacteria-free eludate of the first container may be fed to a second container, the bioreactor, which may contain an active culture or an inoculum. The liquid feed may provide all of the nutritional requirements for cell growth except air. Air may be prefiltered with a microporous filter to remove any contaminating organisms and thereafter introduced into the bioreactor through a submerged diffuser system. The spent air may exit the bioreactor through a connection in the head plate. Algae may be harvested from the bioreactor, preferably in a semi-batch mode into a third zooplankton or shellfish rearing container.

Solid waste disposal is a common problem in animal husbandry in agriculture and aquaculture and often imposes an economic penalty. In the food-fish-waste process of the present invention the problem can be converted into a benefit by converting the waste into nutrient for algae through a catabolization process. Catabolization is achieved by treating the waste with enzymes preferably acidic conditions. The solid waste from the rearing tanks maybe accumulated and periodically treated in batches in a stirred vessel with enzymes and acid. The enzyme is typically a multi-enzyme complex such as Viscozyme® L, a product of Novo Nordisk. Viscozyme L™ is an extract of Aspergillus and is a multienzyme complex containing a wide range of carbohydrases including arabanase, cellulase, betaglucanase, hemicellulase and xylanase. Acidic conditions, for example in a range of pH 3.5 to 5.0, may be achieved by the addition of mineral acid or by the introduction of gaseous carbon dioxide which can be recovered from the bioreactor off gas. The treated waste is filtered to remove undissolved solids. The filtrate may be cycled to the algae growth system for use as a component of the culture media. The quantity of undissolved solids is dependent on the nature of the food provided to the fish. Live, natural foods that aquatic animals consume in nature result in solid wastes that can be catabolized at high conversions by benithic bioreactions. Grain based foods result in significant amounts of undissolved solids typical of wastes produced by hogs and chickens fed with meals made from soy beans and corn.

EXAMPLES

Example 1

Sterilizable Bag System Bioreactor

The bioreactor of the present invention may be understood by reference to FIG. 1 which illustrates the bioreactor assembly in terms of a cross-sectional schematic. The components of the bioreactor envelope are the bag 1 and the head plate assembly which is comprised of the head plate 2, the hold down ring 3, a flat gasket 4, screws 5, an "O" ring gasket 6, a circumferential clamp 7, and an instrument probe 18.

The bag may be fabricated from a polyolefin film preferably $4/1000$ inches thick or greater and autoclavable at 121° C. for 45 minutes in steam heat without degrading. A pattern is drafted onto the film stock, the pattern is cut out and the bag envelope is closed leaving an open top. An impulse sealer that will form a seal $5/1000$ inch wide or greater may be used to seal the bag 1.

The head plate 2 and the hold down ring 3 maybe cut from plastic sheet stock or an impervious metal. Preferably the head plate 2 is $3/8$ inch thick or greater and composed of polypropylene. Apertures 19 for incoming streams, outgoing streams and instrument probes 18 may be drilled through the head plate 2. Holes to receive the screws 5 maybe drilled and tapped.

Sections of flexible tubing 8, preferably of the Pharmed® specification, a proprietary formulation of Norton Performance Plastics Corp., may be inserted into the apertures. A firm nipple 9 preferably fabricated from glass, polymer or an impervious metal may be force-fitted into the inside of the flexible tubing 8 insert for those apertures 19 to be used for incoming and outgoing streams. An instrument probe 18 may be fitted into the flexible tubing 8 insert to take measurements of culture temperature, dissolved oxygen or oxidation/reduction potential.

A bubbler assembly consisting of an air supply tube 10, a diffuser 11, and a shroud 12 is assembled for attachment to the bottom side of the air supply nipple 13. The air supply tube passes through the shroud 12 and attaches to the diffuser 11. The diffuser 11 may be composed of sintered glass, microporous metal, microporous membrane or a combination of these. In applications where microporous diffusers are employed a second supply of air is required to provide sufficient air volume to impel circulation of the culture. The shroud 12 may be fabricated from a flat plastic sheet, preferably 1/16 inch thick polypropylene. The shroud 12 may be fastened together with screws made of suitable plastic or impervious metal. The shroud 12 may have a wide bottom and may taper into a standpipe that directs the bubbles upward and creates an internal liquid flow utilizing the airlift principal. A wing may be placed at the top of the shroud to hold the shroud in a vertical position relative to the sides of the bag.

The bubbler assembly is fixed to the bottom of the head plate by fitting the air supply tube 10 to the bottom of the air inlet nipple 13. Then the "O" ring gasket 6 is placed into a groove around the circumference of the head plate 2.

Inserting the bubbler assembly into the bag 1 and then slipping the head plate 2 into the open end of the bag 1 begins bag closure. The open end of the bag 1 may have a diameter that may be approximately 2 percent less than the diameter of the top plate, creating a stretch-fit bag-to-headplate. The head plate 2 may be pushed into the bag 1. The flat gasket 6 may be coated with silicone sealer and placed on the top of the head plate 2. The end of the bag 1 may be flapped over the gasket 6 and the hold-down ring 3 may be used to secure the closure. The hold-down ring 3 secured with screws 5 that puncture the flap-over and fasten into tapped holes 14 in the head plate 2.

The seal between the "O" ring 6 and the bag 1 may be secured by placing and tightening a clamp 7, preferably made of metal, around the top circumference.

Tubing 8 connections may be fastened to the nipples 9 extending from the apertures 19 for incoming and outgoing fluids.

The resulting bag assembly may be folded up and placed into an autoclave for sterilizing.

The bioreactor may be operated while suspended in a fluid bath that is contained in a vessel 15 designed to withstand the hydrostatic pressure of the bath. The tubing connections of the sterilized bag may be connected with sterile connectors to other processing equipment depending on the process configuration and then the bag may be placed into the vessel 15. The bag contents and bath fluid may be added concurrently in a fashion to maintain the liquid level of the contents and of the bath about even. In that fashion the bag is filled. Air is introduced to the culture through the diffuser 11. The temperature of the bath may be regulated by the action of the heating or cooling element 16. The culture may be irradiated by an external light source 17.

Once operating parameters are set and the system is inoculated, the bioreactor can be operated in batch, semi-batch or continuous mode for 6 months or more.

Example 2
Cell Production System

The present invention as it pertains to a production system for unicellular organisms may be understood by reference to FIG. 2 which shows the production system, including the bioreactor, in terms of a schematic process flow diagram.

The principal vessels of the production system are the inoculum vessel 20, the media vessel 21, the bioreactor 22, and the product vessel 23. The media vessel 21 and the product vessel 23 are depicted as bags submerged in a bath. These two vessels may be as shown or alternatively of more conventional design. The inoculum vessel 20 is depicted as a conventional vessel, however, this vessel may also be a bag submerged in a bath. The process configuration shown can be operated in batch, semi-batch modes or continuous.

Those vessels that are bags submerged in a bath may be assembled as discussed in Example 1. The bioreactor 22 may be assembled with an internal bubbler assembly Each bag assembly can be sterilized individually, or, the bags can be connected, folded up and sterilized as an intact system.

Media may be prepared by introducing media components through the addition connections 24. Although 3 connections 24 are shown there may be more or less. Preferably each of the media component additions are individually filtered. New media components may be added to the media vessel 21 and circulated through the circulating loop 25 using the media pump 26. Media components may be sterilized using the microporous filter 27. Other sterilization techniques known in the art may be used, but a microporous filter 27 is preferred. Sterilized media may be added to the bioreactor through the media charge line 28.

The culture may be initiated by introduction of live cells from the inoculum vessel 20 to the bioreactor by pumping inoculum through the inoculum feed line 29 using the inoculum feed pump 30.

Air or oxygen may be added to the system through a microporous inlet filter 31, which may be a hydrophobic filter with a pore diameter of 0.2 micron or less. Air or oxygen may be introduced into the bioreactor through the gas inlet line 32. Exit gas may pass through the gas outlet line 33 and through the vent filter 34 and thereafter to the atmosphere.

Cells may be harvested from the bioreactor 22 through the product withdrawal connection 35 that extends to the bottom of the bioreactor 22. The transfer may be made by the action of product transfer pump 36 through the product transfer line 37 to the product vessel. Product may be withdrawn as needed from the product vessel 23 using the product pump 38 through the product line 39.

Example 3
Food-Fish-Waste Process System

The present invention, as it pertains to the commercial food-fish-waste aquaculture process, may be understood by reference to FIG. 3 which shows a schematic flow diagram of the commercial food-fish-waste process including the production system for unicellular organisms.

The food-fish-waste process may comprise five subsystems: the cell production system 40, the shellfish rearing system 41, the zooplankton rearing system 42, the fish rearing system 43, and the solid waste catabolization system 44.

Algae cells may be produced from fresh media introduced via the fresh media line 45, purge water from the rearing systems 41 may be introduced through the purge water header 46, and nutrient may be recovered from solid waste and may be introduced through the recovered nutrient line 47. Algae product may be transferred to the shellfish rearing system 41 and the zooplankton system 42 via the algae transfer line 48.

Because algae may be used to nourish shellfish, product 49 may be mature shellfish, ready for consumption, or product 49 may be juveniles which may be removed from the system for further growth elsewhere. For example, juveniles may subsequently be grown in a natural environment. The rearing system 41 may produce both a liquid purge and solid waste. Liquid purge, having a daily volume may be in the range of 2 to 10 percent of the total volume of water contained in the rearing system, 41 may be removed to the rearing system purge header through discharge line 50.

Solid waste produced by both the shellfish and the biofilter may be removed to the rearing system solid waste header 51 through discharge line 52.

Algae may be the food for zooplankton at all stages of zooplankton life cycle. The zooplankton product 53 may be grown to the maturity required for use as feed by the animals in the fish rearing system 43. The zooplankton rearing system 42 may produce both a liquid purge and solid waste. Liquid purge whose daily volume is in the range of 2 to 10 percent of the total volume of water contained in the rearing system 42 may be transferred to the rearing system purge header through discharge line 54. Solid waste produced in the rearing systems shown in FIG. 3 may be removed to the rearing system solid waste header 51 through the discharge lines 50, 55 and 58.

Zooplankton may be the food for juvenile fish, however larger fish require supplemental feeding. The fish product 56 may be aquatic animals that feed on zooplankton including finfish and crustaceans. The fish rearing system 43 may produce both a liquid purge and solid waste. Liquid purge, having a daily volume is in the range of 2 to 10 percent of the total volume of water contained in the rearing system 43, may be removed to the rearing system purge header through discharge line 57. Solid waste produced in the shellfish rearing system 49 may be removed to the rearing system solid waste header 51 through discharge line 58.

Solid wastes may be collected and transferred to the solid waste catabolization system 44 through the solid waste header. The wastes collected may be treated with enzymes and acidification to produce nutrients for the algae and to reduce the amount of solid wastes. Supplemental feeding in the fish rearing system will increase the fraction of waste that cannot be catabolized. Algae nutrient may be transferred to the cell production system 40 through the recovered nutrient line 47. Waste may be removed through discharge line 20.

What is claimed is:

1. A unicellular culture system comprising:
    an autoclavable bioreactor including:
        a) flexible, light transmitting walls defining an interior space and having an opening;
        b) an oxygen diffusor situated in the interior space; and
        c) a head plate, associated with the opening, the head plate having a plurality of apertures.

2. The culture system of claim 1, further comprising a rigid support bath external to said bioreactor.

3. The culture system of claim 2, further comprising at least one vessel selected from the group consisting of an inoculum vessel, a media vessel, and product vessel, wherein said vessel or vessels are connected to said head plate.

4. The culture system of claim 3, wherein the support bath provides temperature control.

5. A cell production system comprising the culture system of claim 3 wherein one vessel is an inoculum vessel and said inoculum vessel is connected to said bioreactor such that the system can be operated in batch, semi-batch or continuous mode.

6. A fish or shellfish rearing system comprising a rearing tank connected to the culture system of claim 1.

7. The rearing system of claim 6, wherein algae are provided as a source of nutrients for fish or shellfish in the rearing tank.

8. The rearing system of claim 7, wherein the algae are *Tetraselmis chuii*.

9. The rearing system of claim 7, wherein the fish or shellfish are selected from the group consisting of *Penaeus vannamei, Penaeus monodon, Crossostrae Virginicus, Crossotrae gigas, Pinctada maxima, Pinctada margaritifera, Pinctada fucata,* and *Argopectin irradians*.

10. The rearing system of claim 7, wherein the algae are provided with wastes produced by the fish or shellfish as a source of nutrients.

11. The rearing system of claim 10, further comprising a rearing tank for zooplankton wherein the zooplankton are used as a source of nutrients for the fish.

12. The rearing system of claim 11 wherein the zooplankton are Artemia.

13. The system according to claim 1, wherein said oxygen diffusor is capable of difflusing air.

14. A unicellular culture system comprising:
    an autoclavable bioreactor including:
        a) flexible, light transmitting walls defining an interior space and having an opening;
        b) a difflusor, for a gas containing oxygen, situated in the interior space; and
        c) a head plate, associated with the opening, the head plate having a plurality of apertures.

15. The system according to claim 14, wherein said diffusor is capable of diffusing air.

* * * * *